(12) United States Patent
O'Lenick, Jr.

(10) Patent No.: US 6,649,578 B1
(45) Date of Patent: Nov. 18, 2003

(54) DI-CARBOXY ALKYL PHOSPHATE ESTERS IN PERSONAL CARE APPLICATIONS

(75) Inventor: Anthony J. O'Lenick, Jr., Dacula, GA (US)

(73) Assignee: Applied Carbo Chemicals Inc., E. Lansing, MI (US)

( * ) Notice: Subject to any disclaimer, the term of this patent is extended or adjusted under 35 U.S.C. 154(b) by 0 days.

(21) Appl. No.: 10/113,181

(22) Filed: Apr. 1, 2002

Related U.S. Application Data

(63) Continuation-in-part of application No. 09/611,814, filed on Jul. 7, 2000, now Pat. No. 6,365,774, which is a continuation-in-part of application No. 09/611,429, filed on Jul. 7, 2000, now Pat. No. 6,229,038, which is a continuation-in-part of application No. 09/493,172, filed on Jan. 28, 2000, now Pat. No. 6,346,648.

(51) Int. Cl.$^7$ .................. A61K 7/075; A61K 7/078; A61K 7/50; C11D 1/34

(52) U.S. Cl. ............... 510/122; 424/70.23; 510/135; 510/158; 510/436

(58) Field of Search .................. 510/122, 135, 510/435, 158, 436; 424/70.23

(56) References Cited

U.S. PATENT DOCUMENTS

| | | | | | |
|---|---|---|---|---|---|
| 2,192,907 | A | * | 3/1940 | Harris | 510/479 X |
| 2,942,013 | A | * | 6/1960 | Bruson et al. | 516/75 X |
| 3,594,409 | A | * | 7/1971 | LaChampt et al. | 516/75 X |
| 3,954,858 | A | * | 5/1976 | Lamberti et al. | 562/583 |
| 4,020,101 | A | * | 4/1977 | Geffers et al. | 252/180 X |
| 4,065,475 | A | | 12/1977 | Hosoi et al. | |
| 4,152,515 | A | * | 5/1979 | Lamberti et al. | 510/479 X |
| 4,479,893 | A | * | 10/1984 | Hirota et al. | |
| 4,654,159 | A | * | 3/1987 | Bush et al. | 510/479 X |
| 4,827,028 | A | * | 5/1989 | Scardera et al. | 510/479 X |
| 4,832,872 | A | | 5/1989 | Scandel | |
| 4,954,341 | A | * | 9/1990 | Nakamura et al. | 424/70.23 |
| 5,071,585 | A | * | 12/1991 | Matsunaga et al. | |
| 5,120,464 | A | * | 6/1992 | Kamegai et al. | |
| 5,139,781 | A | * | 8/1992 | Birtwistle et al. | 424/401 |
| 5,334,387 | A | * | 8/1994 | Haugk | 424/401 |
| 5,739,092 | A | * | 4/1998 | Ofosu-Asante | 510/434 X |
| 6,365,774 | B1 | * | 4/2002 | O'Lenick, Jr. | 562/583 |

* cited by examiner

*Primary Examiner*—Richard D. Lovering

(57) ABSTRACT

The present invention relates to a process for cleaning and conditioning hair and skin, which comprises contacting the hair or skin with an effective cleansing amount of a phosphate amphoteric. Reacting epoxy succinic acid and a salt of an alkyl phosphate ester under aqueous conditions make the compounds of the present invention.

15 Claims, No Drawings

DI-CARBOXY ALKYL PHOSPHATE ESTERS IN PERSONAL CARE APPLICATIONS

RELATED APPLICATION

This application is a continuation-in-part of application Ser. No. 09/611,814 filed Jul. 7, 2000, now U.S. Pat. No. 6,365,744, which is in turn a continuation-in-part of application Ser. No. 09/611,429 filed Jul. 7, 2000, now U.S. Pat. No. 6,229,038, which is in turn a continuation-in-part of application Ser. No. 09/493,172 filed Jan. 28, 2000, now U.S. Pat. No. 6,346,648.

BACKGROUND OF THE INVENTION

1. Field of Invention

The present invention relates to a personal care use of (a) novel di-carboxy phosphate ester.

The compounds of the present invention are made by reacting epoxy succinic acid and a salt of an alkyl phosphate ester under aqueous conditions. The resulting compound is quite stable very mild to hair and skin and offers excellent surfactant properties, including detergency and foam. In addition, compounds of the present invention containing a pendant hydroxyl group which alters the water solubility and emulsification properties of the compound.

The compounds of the present invention are used in a process for cleaning and conditioning hair and skin, which comprises contacting the hair or skin with an effective cleansing amount of the compounds of the present invention.

2. Object of the Invention

It is the object of the present invention to provide novel a process for the preparation of surface-active agents that are well tolerated by skin and eyes. These non-irritating products produce copious foam, have outstanding emulsification properties and are ideal products for use in the formulation of hair and skin care products like shampoos, conditioners and body washes.

DESCRIPTION OF THE ARTS AND PRACTICES

U.S. Pat. No. 4,065,475 to Hosi et al issued in December of 1977 discloses a process for preparation of cis-epoxy succinic acid, a raw material for the preparation of the compounds of the present invention. This material is easily made by the reaction of maleic acid with hydrogen peroxide in the presence of a tungsten catalyst. The availability of this high purity raw material is very critical in the preparation of the compounds of the present invention.

THE INVENTION

Summary of the Invention

The compounds of the present invention are made by reacting cis-epoxy succinic acid with a salt of an alkyl phosphate ester under aqueous conditions. The resulting compound is an outstanding surfactant for personal care applications.

The compounds of the present invention are used in a process for cleaning and conditioning hair and skin, which comprises contacting the hair or skin with an effective cleansing amount of a phosphate amphoteric conforming to the following structure:

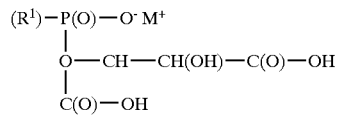
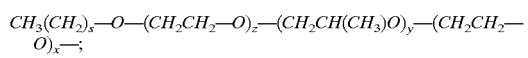

wherein;

$R^1$ is:

$$CH_3(CH_2)_s\text{—}O\text{—}(CH_2CH_2\text{—}O)_z\text{—}(CH_2CH(CH_3)O)_y\text{—}(CH_2CH_2\text{—}O)_x\text{—};$$

s is an integer ranging from 3 to 21;
x, y and z are independently integers ranging from 0 to 20;
M is selected from the group consisting of H, Na, K, Li, and $NH_4$.

DETAILED DESCRIPTION OF THE INVENTION

The compounds of the present invention have several key portions in the molecule. Those groups include (a) an alkyl phosphate group, (b) a hydroxy linkage group and (c) two carboxy groups that improve water solubility. These groups and their positioning in the molecule result in unique properties for the molecule. These include foam, detergency, chelation properties (especially for calcium ion), emulsification properties, wetting properties, particularly for hydrophobic pigments, and a lubricious skin feel. This combination of properties has heretofore been unattainable in one molecule.

Compounds useful in the process of the present invention conform to the following structure:

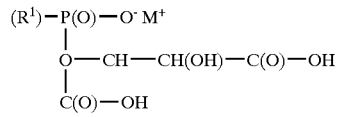
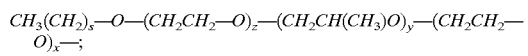

wherein;

$R^1$ is:

$$CH_3(CH_2)_s\text{—}O\text{—}(CH_2CH_2\text{—}O)_z\text{—}(CH_2CH(CH_3)O)_y\text{—}(CH_2CH_2\text{—}O)_x\text{—};$$

s is an integer ranging from 3 to 21;
x, y and z are independently integers ranging from 0 to 20;
M is selected from the group consisting of H, Na, K, Li, and $NH_4$.

The effective cleansing amount ranges from 0.1% to 25% by weight, with a concentration of between 1 and 10% by weight being preferred.

Illustrative of the sequence for the preparation of the compounds of the present is as follows;

In a 30% aqueous solution the disodium salt of a phosphate ester (pH 10.4) is reacted with an epoxy succinic acid to produce the phosphate ester of the present invention:

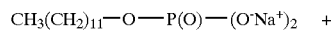
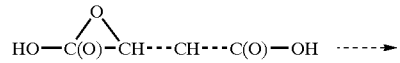

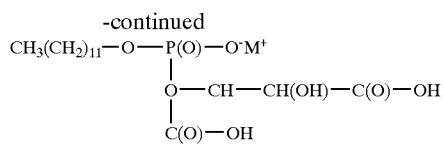

$$CH_3(CH_2)_{11}-O-P(O)-O^-M^+$$
with O—CH—CH(OH)—C(O)—OH and C(O)—OH branches

The compounds of the present invention are very good ingredients in a variety of applications due to the presence of both the phosphate and the two carboxyl groups. These personal care applications include hair and skin cleansers, bubble bath compositions, and hair conditioners.

Preferred Embodiments

The effective cleansing amount ranges from 0.1% to 25% by weight, with a concentration of between 1 and 10% by weight being preferred. In a preferred embodiment s is 3.

In a preferred embodiment s is 5.
In a preferred embodiment s is 7.
In a preferred embodiment s is 9.
In a preferred embodiment s is 11.
In a preferred embodiment s is 13
In a preferred embodiments is 16.
In a preferred embodiment x, y, and z are each zero.
In a preferred embodiment x ranges from 3 to 10.
In a preferred embodiment y ranges from 1 to 10.
In a preferred embodiment s is 11 and x ranges from 3 to 10.
In a preferred embodiment s is 13 and x ranges from 3 to 10.
In a preferred embodiment s is 15 and x ranges from 3 to 10.

EXAMPLES

Raw Materials

Epoxy Succinic Acid

U.S. Pat. No. 4,065,475 to Hosi et al issued in December of 1977 discloses a process for preparation of cis-epoxy succinic acid, a raw material for the preparation of the compounds of the present invention.

Epoxy succinic acid is commercially available from a variety of sources and conforms to the following structure:

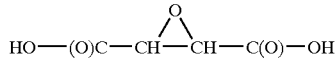

$$HO-(O)C-CH-CH-C(O)-OH$$ (with epoxide O bridging)

Phosphate Esters

The phosphate esters useful. as intermediates for the preparation of the compounds present invention are commercially available from Siltech LLC, Dacula Ga.

They conform to the following structure:

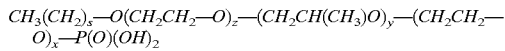

$$CH_3(CH_2)_s-O(CH_2CH_2-O)_z-(CH_2CH(CH_3)O)_y-(CH_2CH_2-O)_x-P(O)(OH)_2$$

wherein;

s is an integer ranging from 3 to 21;
x, y and z are integers and are independently ranging from 0 to 20.

Phosphate Ester Examples

| Example | s | x | y | z |
|---|---|---|---|---|
| 1 | 3 | 0 | 0 | 0 |
| 2 | 5 | 0 | 0 | 0 |
| 3 | 7 | 0 | 0 | 0 |
| 4 | 9 | 0 | 0 | 0 |
| 5 | 11 | 0 | 0 | 10 |
| 6 | 17 | 0 | 0 | 10 |
| 7 | 3 | 0 | 0 | 0 |
| 8 | 5 | 10 | 1 | 20 |
| 9 | 9 | 15 | 20 | 5 |
| 10 | 11 | 20 | 3 | 10 |
| 11 | 17 | 20 | 20 | 20 |
| 12 | 21 | 1 | 10 | 20 |

Preparation of the Products of The Present Invention

General Procedure

Into a suitable vessel equipped with thermometer, agitation and heating capabilities is added the specified amount of water. Next the specified amount of phosphate ester is added under good agitation. The pH is adjusted to 10.3 with the specified base. The reaction mass is heated to 70–80° C. and the epoxy succinic is added over 1 hour. The exotherm . is watched so that the temperature does not exceed 95° C. The pH is kept between 8–9 by addition of base. If that temperature is reached, cooling is applied and the addition suspended.

After the addition is complete the reaction mass is held at between 80–90° C. for four hours. During that time the % epoxide becomes vanishingly low.

Examples 13–24

Example 13

Into a suitable vessel equipped with thermometer, agitation and heating capabilities is added 500.0 grams of water. Next add 171.0 grams of phosphate ester (Example 1) under good agitation. The pH is adjusted to 10.3 with the KOH. The reaction mass is heated to 70–80° C. Next add 132.0 grams of epoxy succinic acid (example 1). Addition is made over a 1 hour time period. The exotherm is watched so that the temperature does not exceed 95° C.

After the addition is complete the reaction mass is held at between 80–90° C. for four hours. During that time the % epoxide becomes vanishingly low.

Examples 14–24

Example 13 is repeated, only this time the specified amount of water is added, and the specified quantity and type of phosphate ester is added replacing the quantity and type in example 13.

| Example | Phosphate Ester Example | Grams | Water Grams | Base Type |
|---|---|---|---|---|
| 13 | 1 | 171.0 | 250.0 | KOH |
| 14 | 2 | 199.0 | 400.0 | KOH |
| 15 | 3 | 227.0 | 500.0 | NaOH |
| 16 | 4 | 255.0 | 500.0 | NaOH |
| 17 | 5 | 723.0 | 1400.0 | KOH |
| 18 | 6 | 807.0 | 2000.0 | NaOH |
| 19 | 7 | 171.0 | 342.0 | KOH |
| 20 | 8 | 1578.0 | 3000.0 | KOH |
| 21 | 9 | 2315.0 | 5000.0 | KOH |
| 22 | 10 | 1780.0 | 3200.0 | KOH |

-continued

| Example | Phosphate Ester Example | Grams | Water Grams | Base Type |
|---|---|---|---|---|
| 23 | 11 | 3307.0 | 6614.0 | NaOH |
| 24 | 12 | 2567.0 | 5000.0 | NaOH |
| 25 | 12 | 2567.0 | 5000.0 | NaOH |
| 26 | 11 | 3307.0 | 6700.0 | KOH |
| 27 | 10 | 1780.0 | 3200.0 | LiOH |
| 28 | 9 | 2315.0 | 3900.0 | KOH |
| 29 | 8 | 1578.0 | 7530.0 | NH₄OH |
| 30 | 1 | 171.0 | 250.0 | KOH |
| 31 | 2 | 199.0 | 400.0 | KOH |
| 32 | 3 | 227.0 | 500.0 | NaOH |
| 33 | 4 | 255.0 | 500.0 | NaOH |
| 34 | 5 | 723.0 | 1400.0 | KOH |
| 35 | 6 | 807.0 | 2000.0 | NaOH |

The compounds of the present invention are in aqueous solution or emulsion and generally range from 20–60% solids. The preferred range is 30–40% solids. The products are used without purification.

Applications

Typical Formulations

The compounds of the present invention are generally formulated into shampoos, bubble baths and shower gels. The formulations contain water, an anionic surfactant, commonly fatty alcohol sulfates or preferably fatty alcohol ether sulfates having 1 to 4 moles of polyoxyethylene groups present, between 0.01 and 10.0% by weight of the compounds of the present invention, and optionally, dimethicone copolyol, cocamidopropyl betaine, alkanolamids, polysorbates and antimicrobials, like for example Triclosan.

Specific Formulation Examples

CLEAR SOFTENING SHAMPOO

| INGREDIENTS | PERCENT |
|---|---|
| A. Deionized Water | QS to 100.00 |
| Sodium Laureth Sulfate | 30.00 |
| Cocamide DEA | 2.50 |
| Cocamidopropyl Betaine | 7.00 |
| Dimethicone Copolyol | 2.00 |
| Example 18 | 1.50 |
|  | 6.50 |
| B. Quaternium-15 | 0.20 |
| C. Citric Acid 50% Solution | QS |

PROCEDURE

1. In a suitable container, combine all ingredients together of Phase A with good agitation, mix without aerating. Begin to heat to 70–75° C. When clear and uniform, stop heating and cool to 35–40° C.
2. Add Phase B. Mix well.
3. Add Phase C. Adjust pH to 6.3–6.8.

MILK FACIAL SCRUB

| INGREDIENTS | PERCENT |
|---|---|
| A. Deionized water | Qs to 100.00 |
| Sodium laureth sulfate | 30.00 |
| Cocamid DEA | 2.50 |
| Cocamidopropyl betaine | 7.00 |
| Dimethicone copolyol | 1.00 |
| Example 20 | 3.00 |
| B. Chamomile Extract | 1.00 |
| Mallow Extract | 1.00 |
| Cucumber Extract | 1.00 |
| C. Jojoba Beads | 5.00 |
| D. Germaben II | 1.00 |
| Fragrance | 0.50 |

PROCEDURES

1. In a suitable container, add water and begin to heat to 7–75° C.
2. Add remaining ingredients of phase A, one at a time.
3. Mixwell
4. Cool to 30–35° C., add phase B mix well,
5. Add phase C, mix without aerating
6. Add phase D, mix until uniform.

BODY WASH

| INGREDIENTS | PERCENT |
|---|---|
| A. Deionized Water | QS to 100.00 |
| Sodium Laureth Sulfate | 30.00 |
| Cocamidopropyl Betaine | 7.00 |
| Methylparaben | 0.15 |
| Propylparaben | 0.05 |
| Example 20 | 1.50 |
| Cocamide DEA | 3.00 |
| Eethylene glycol distearate | 2.50 |
| Dimethicone Copolyol | 2.00 |
| B. Imidazolidinyl Urea | 0.30 |
| Cirtric Acid/TEA | QS |
| C. Cucumber Extract | 0.25 |
| Elder Extract | 0.25 |
| Matricaria Extract | 0.25 |
| Ginkgo Extract | 0.25 |
| D. Fragrance | 0.50 |

PROCEDURE

1. In a suitable container, weigh and add all the ingredients of Phase A one at a time with good agitation.
2. Begin to beat to 75–80° C. Mix until uniform.
3. Begin to cool to 40–45° C. Add Phase B, then Phase C. Mix well.
4. Add Phase D.
5. Mix well. Cool to 35° C.

SKIN CONDITIONING BUBBLE BATH

| INGREDIENTS | PERCENT |
|---|---|
| A. Dionized Water | QS to 100.00 |
| Decyl Polyglucose (and) Ammonium Laureth Sulfate | 18.00 |
| Cocamidopropyl sultaine | 5.00 |
| Cocamidopropyl Betaine | 3.00 |
| Cocamide DEA | 2.50 |
| B. Example 13 | 5.00 |
| C. Complex Aligomarin | 2.00 |
| D. Preservative | 1.00 |
| E. QS Fragrance and Color | QS |

PROCEDURE

1. Combine ingredients in Phase A and heat to 45–50° C. with careful mixing.
2. When all ingredients are melted and uniform, add Phase B. Mix well.
3. Cool to 35° C. Add Phase C while mixing
4. Add Phase D then Phase E. Mixing carefully.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A process for cleaning and conditioning hair and skin, which comprises contacting the hair or skin with an effective cleansing amount of an aqueous solution or emulsion of a phosphate amphoteric conforming to the following structure:

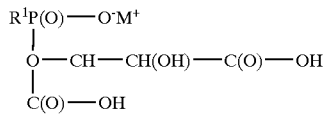

wherein:

$R^1$ is:

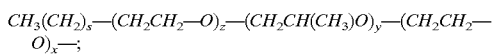

s is an integer ranging from 3 to 21;
x, y and z are independently integers ranging from 0 to 20;
M is selected from the group consisting of H, Na, K, Li, and $NH_4$.

2. A process of claim 1 wherein the effective cleansing amount ranges from 0.1% to 25% by weight.
3. A process of claim 1 wherein the effective cleansing amount ranges from 1% and 10% by weight.
4. A process of claim 1 wherein s is 3.
5. A process of claim 1 wherein s is 5.
6. A process of claim 1 wherein s is 7.
7. A process of claim 1 wherein s is 9.
8. A process of claim 1 wherein s is 11.
9. A process of claim 1 wherein s is 13.
10. A process of claim 1 wherein s is 17.
11. A process of claim 1 wherein s is 19.
12. A process of claim 1 wherein s is 21.
13. A process of claim 1 wherein x, y, and z are each zero.
14. A process of claim 1 wherein x ranges from 3 to 10.
15. A process of claim 1 wherein y ranges from 1 to 10.

* * * * *